(12) United States Patent
Kojima

(10) Patent No.: US 9,866,738 B2
(45) Date of Patent: Jan. 9, 2018

(54) MANUFACTURING METHOD OF SEMICONDUCTOR APPARATUS, SEMICONDUCTOR APPARATUS, AND ENDOSCOPE

(71) Applicant: OLYMPUS CORPORATION, Tokyo (JP)

(72) Inventor: Kazuaki Kojima, Suwa (JP)

(73) Assignee: Olympus Corporation, Tokyo (JP)

( * ) Notice: Subject to any disclaimer, the term of this patent is extended or adjusted under 35 U.S.C. 154(b) by 243 days.

(21) Appl. No.: 14/793,111

(22) Filed: Jul. 7, 2015

(65) Prior Publication Data

US 2015/0312457 A1    Oct. 29, 2015

Related U.S. Application Data

(63) Continuation of application No. PCT/JP2013/074691, filed on Sep. 12, 2013.

(30) Foreign Application Priority Data

Jan. 11, 2013   (JP) ................... 2013-003845

(51) Int. Cl.
*A61B 1/04*    (2006.01)
*H04N 5/225*   (2006.01)
(Continued)

(52) U.S. Cl.
CPC ......... *H04N 5/2257* (2013.01); *A61B 1/0011* (2013.01); *A61B 1/00124* (2013.01); *A61B 1/051* (2013.01); *G02B 23/2484* (2013.01); *H04N 5/2253* (2013.01); *H04N 5/369* (2013.01); *H05K 1/021* (2013.01); *H05K 1/181* (2013.01); *H05K 1/189* (2013.01);
(Continued)

(58) Field of Classification Search
None
See application file for complete search history.

(56) References Cited

U.S. PATENT DOCUMENTS

2010/0201794 A1    8/2010   Kido et al.

FOREIGN PATENT DOCUMENTS

JP    2009-082503 A    4/2009
JP    2011-200401 A    10/2011
(Continued)

OTHER PUBLICATIONS

International Search Report dated Oct. 22, 2013 issued in PCT/JP2013/074691.

*Primary Examiner* — James M Anderson, II
(74) *Attorney, Agent, or Firm* — Scully, Scott, Murphy & Presser, P.C.

(57) ABSTRACT

A manufacturing method of an image pickup apparatus includes a step of manufacturing an image pickup device chip, a step of manufacturing a wiring board having first terminals and second terminals disposed on both sides of a first primary surface with a central flexible portion intervened in between, a step of joining a heat conductive block to a second primary surface of the wiring board, a step of joining the image pickup device chip to the first terminals of the wiring board, a step of performing solder joining of core wires of a cable to the second terminals of the wiring board by conducting heat generated by a heat tool through the heat conductive block, a step of bending the wiring board, and a step of performing housing inside a frame member, and sealing with sealing resin.

10 Claims, 8 Drawing Sheets

(51) Int. Cl.
*A61B 1/00* (2006.01)
*A61B 1/05* (2006.01)
*G02B 23/24* (2006.01)
*H04N 5/369* (2011.01)
*H05K 1/02* (2006.01)
*H05K 1/18* (2006.01)
*H05K 3/34* (2006.01)
*H05K 5/04* (2006.01)

(52) U.S. Cl.
CPC ............ *H05K 3/3431* (2013.01); *H05K 5/04* (2013.01); *H05K 2201/055* (2013.01); *H05K 2201/066* (2013.01); *H05K 2201/10121* (2013.01); *H05K 2201/10151* (2013.01); *H05K 2203/1305* (2013.01); *H05K 2203/302* (2013.01)

(56) References Cited

FOREIGN PATENT DOCUMENTS

| | | |
|---|---|---|
| JP | 2012-055570 A | 3/2012 |
| WO | WO 2009041724 A | 4/2009 |

.# MANUFACTURING METHOD OF SEMICONDUCTOR APPARATUS, SEMICONDUCTOR APPARATUS, AND ENDOSCOPE

CROSS REFERENCE TO RELATED APPLICATION

This application is a continuation application of PCT/JP2013/074691 filed on Sep. 12, 2013 and claims benefit of Japanese Application No. 2013-003845 filed in Japan on Jan. 11, 2013, the entire contents of which are incorporated herein by this reference.

BACKGROUND OF INVENTION

1. Field of the Invention

The present invention relates to a manufacturing method of a semiconductor apparatus in which a semiconductor device chip is connected with a signal cable through a wiring board, the semiconductor apparatus, and an endoscope provided with the semiconductor apparatus at a distal end portion of an insertion portion.

2. Description of the Related Art

An image pickup apparatus provided with an image pickup device chip which is a semiconductor device chip is used by being disposed at a distal end portion of an electronic endoscope. Regarding the distal end portion of the electronic endoscope, there is an important issue of reducing a diameter thereof in order to reduce a pain on a patient.

In Japanese Patent Laid-Open Publication No. 2012-55570, an image pickup apparatus 101 as shown in FIGS. 1 and 2 is disclosed. A cover glass 110, which is an optical member, or the like is joined to an image pickup device chip 120 of the image pickup apparatus 101. Further, as shown in FIG. 1, in a manufacturing step of the image pickup apparatus 101, signal cables 150 are joined with solder to a wiring board 130 in a planar state, to which the image pickup device chip 120 is joined. Then, the wiring board 130 is bent by 180 degrees as shown in FIG. 2 and thereby the image pickup apparatus 101 which is thin in diameter is manufactured.

SUMMARY OF THE INVENTION

A manufacturing method of a semiconductor apparatus according to an embodiment of the present invention includes: a step of manufacturing a semiconductor device chip having a semiconductor device unit on an obverse surface and junction terminals on a reverse surface, the junction terminals being connected with the semiconductor device unit via through wirings; a step of manufacturing a wiring board having a rectangular shape and a width smaller than a width of the semiconductor device chip, the wiring board having first terminals and second terminals connected with the first terminals on a first primary surface, the first terminals and the second terminals being disposed on both sides with a flexible portion intervened in between; a step of joining a first junction surface of a heat conductive block to a second primary surface of the wiring board in a second terminal opposing region which is opposite to a region in which the second terminals are disposed on the first primary surface of the wiring board in a planar state, the heat conductive block being made of a material having thermal conductivity not lower than 20 $Wm^{-1}K^{-1}$; a step of joining the junction terminals of the semiconductor device chip to the first terminals of the wiring board in the planar state; a step of performing solder joining of core wires of a signal cable to the second terminals of the wiring board by conducting heat generated by a heat tool, which is heated to have a soldering temperature, through the heat conductive block; a step of bending the wiring board at the flexible portion such that a second junction surface of the heat conductive block which is opposite to the first junction surface comes in contact with the second primary surface of the wiring board, and arranging the wiring board within a projected plane of the semiconductor device chip; and a step of housing the semiconductor device chip, the wiring board, the heat conductive block, and the signal cable, which are integrated, inside a frame member made of metal, and sealing the semiconductor device chip, the wiring board, the heat conductive block and the signal cable with sealing resin.

A semiconductor apparatus according to another embodiment of the present invention includes: a semiconductor device chip having a semiconductor device unit on an obverse surface and junction terminals on a reverse surface, the junction terminals being connected with the semiconductor device unit via through wirings; a signal cable having core wires electrically connected with the semiconductor device unit; a wiring board having a rectangular shape and a width smaller than a width of the semiconductor device chip, the wiring board having first terminals joined to the junction terminals and second terminals connected with the first terminals on a first primary surface, the first terminals and second terminals being disposed on both sides with a flexible portion intervened in between, the second terminals being joined to the core wires of the signal cable by soldering, the wiring board being bent at the flexible portion to be in a state where the first primary surface and the second primary surface are parallel; a heat conductive block sandwiched by the second primary surface of the wiring board that is bent, and made of a material having thermal conductivity not lower than 20 $Wm^{-1}K^{-1}$; and a frame member in which the semiconductor device chip, the wiring board, the heat conductive block and the signal cable are housed, the frame member being made of metal and an inside of the frame member being sealed with sealing resin.

An endoscope according to still another embodiment of the present invention includes an image pickup apparatus at a distal end portion of an insertion portion, the image pickup apparatus including: a semiconductor device chip having an image pickup unit on an obverse surface and junction terminals on a reverse surface, the junction terminals being connected with the image pickup unit via through wirings; a signal cable having core wires electrically connected with the image pickup unit; a wiring board having a rectangular shape and a width smaller than a width of the semiconductor device chip, the wiring board having first terminals joined to the junction terminals and second terminals connected with the first terminals on a first primary surface, the first terminals and second terminals being disposed on both sides with a flexible portion intervened in between, the second terminals being joined to the core wires of the signal cable by soldering, the wiring board being bent at the flexible portion to be in a state where the first primary surface and the second primary surface are parallel; a heat conductive block sandwiched by the second primary surface of the wiring board that is bent, and made of a material having thermal conductivity not lower than 20 $Wm^{-1}K^{-1}$; and a frame member in which the semiconductor device chip, the wiring board, the heat conductive block and the signal cable are housed, the frame member being made of metal and an inside of the frame member being sealed with sealing resin.

DETAILED DESCRIPTION OF THE PREFERRED EMBODIMENT(S)

First Embodiment

Figure 1:
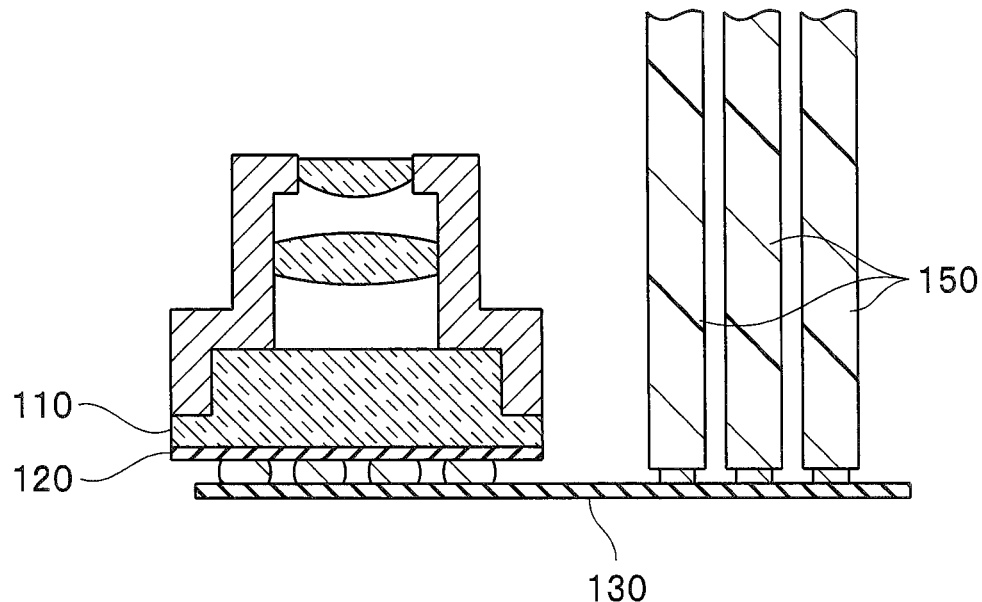
FIG. 1 is a cross sectional view for explaining a conventional manufacturing method of an image pickup apparatus.
Figure 2:
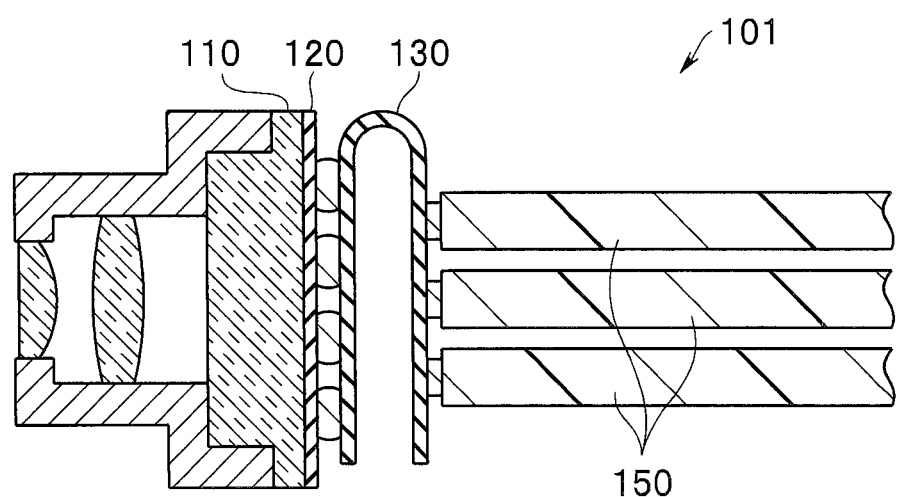
FIG. 2 is a cross sectional view of the conventional image pickup apparatus.
Figure 3:
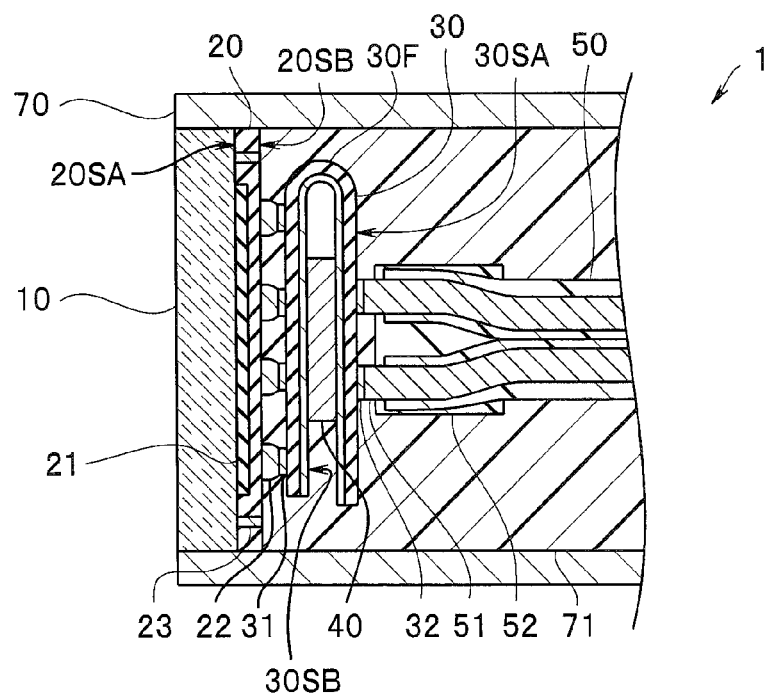
FIG. 3 is a cross sectional view of an image pickup apparatus according to a first embodiment.

As shown in FIG. 3, a semiconductor apparatus according to the embodiment is an image pickup apparatus 1 provided with an image pickup device chip 20 having an image pickup unit 21 formed thereon, as a semiconductor chip.

Figure 4:
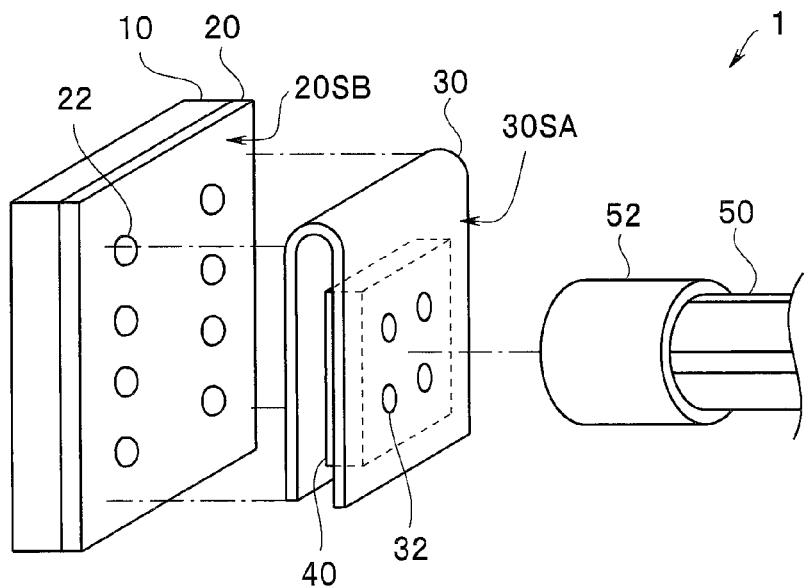
FIG. 4 is an exploded view of the image pickup apparatus according to the first embodiment.

As shown in FIGS. 3 and 4, the image pickup apparatus 1 is provided with a cover glass 10, the image pickup device chip 20, a wiring board 30, a heat conductive block 40, signal cables (hereinafter also referred to as "cable") 50, and a frame member 70. It is noted that the drawings show schematic views for explanation and a ratio of longitudinal and latitudinal dimensions is different from an actual ratio. Further, in the drawings, part of the elements may be omitted, and in the cross sectional views, part of the elements may be shown as viewed from the side. For example, the frame member 70 and other elements are not shown in FIG. 4 which is an exploded view.

The image pickup device chip 20 has the image pickup unit 21 on an obverse surface 20SA and junction terminals 22 on a reverse surface 20SB, the junction terminals 22 being connected with the image pickup unit 21, which is a semiconductor device unit, via through wirings 23. The wiring board 30 has an approximately rectangular shape in which a width, and a length in a state of being bent are smaller than dimensions of the image pickup device chip 20 when viewed in a plan view. The wiring board 30 has first terminals 31 and second terminals 32 which are disposed on both sides thereof on a first primary surface 30SA with a central flexible portion 30F intervened in between, the second terminals 32 being connected with the first terminals 31 by wirings (not shown).

The wiring board 30 is bent at the central flexible portion 30F by 180 degrees so that the first primary surface 30SA and a second primary surface 30SB are in parallel. The first terminals 31 are joined to the junction terminals 22 of the image pickup device chip 20. On the other hand, the second terminals 32 are joined with solder to core wires 51 of the cable 50. Thus, the core wires 51 of the cable 50 are electrically connected with the image pickup unit 21.

A heat conductive block 40 is made of a material having thermal conductivity not lower than 20 $Wm^{-1}K^{-1}$. The heat conductive block 40 is sandwiched by the second primary surface 30SB of the bent wiring board 30.

Further, the image pickup device chip 20, the wiring board 30, the heat conductive block 40 and the cable 50 are housed inside the frame member 70, which is made of metal, and sealed with sealing resin 71. The frame member 70 is a hollow prism having openings on both end faces. Inner dimensions of the frame member 70 are substantially the same as outer dimensions of the image pickup device chip 20. The other end of the cable 50 is connected with a signal processing apparatus or the like which is not shown.

It is noted that the plurality of cables 50 are bundled by a binding member 52 so that positions of the core wires 51 exposed at distal end portions meet arrangement positions of the plurality of second terminals 32.

In the image pickup apparatus 1, heat generated by the image pickup device chip 20 is transmitted also to the cable 50 through the heat conductive block 40. Therefore, the image pickup apparatus 1 is stable in operation in comparison with a conventional image pickup apparatus without a heat conductive block.

Figure 5:
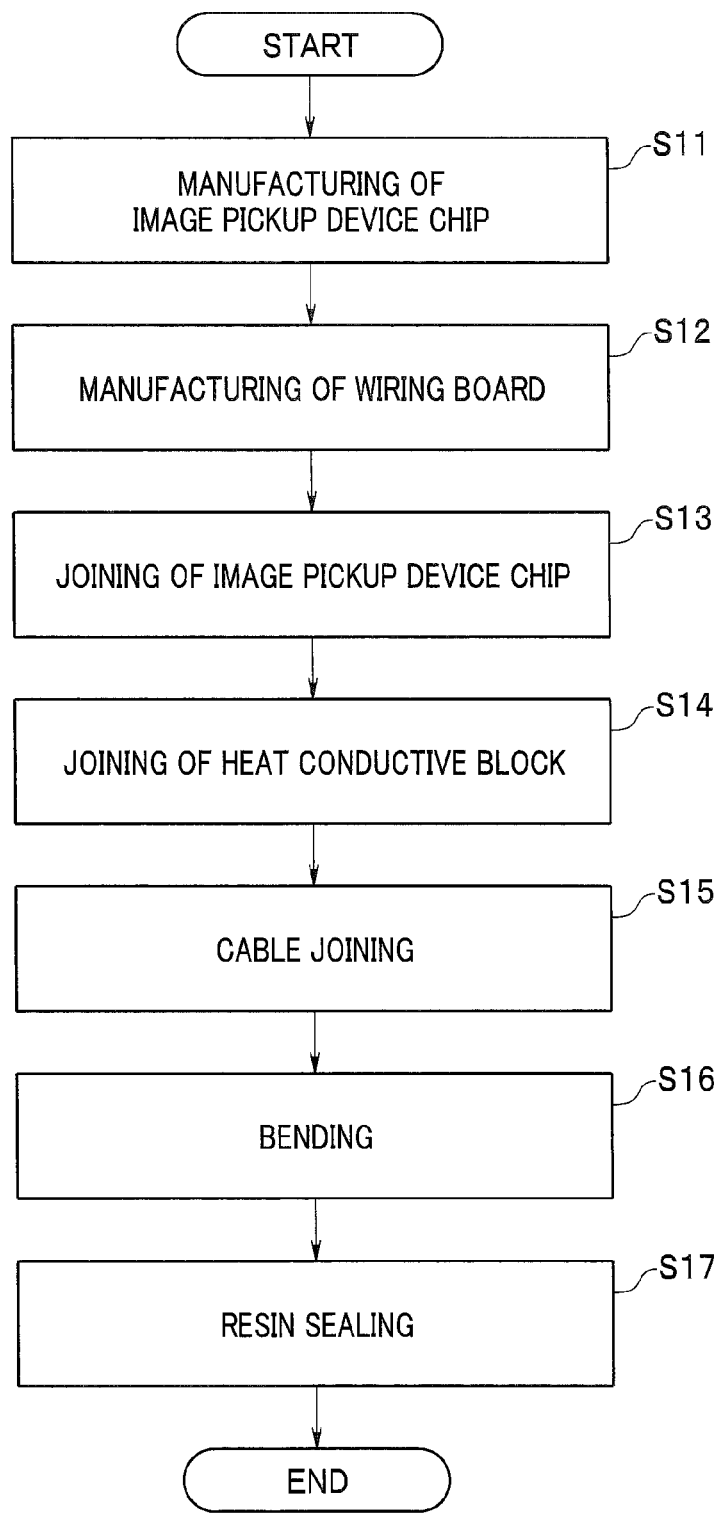
FIG. 5 is a flowchart for explaining a manufacturing method of the image pickup apparatus according to the first embodiment.

Next, a manufacturing method of the image pickup apparatus 1 will be described along the flowchart shown in FIG. 5.

<Step S11> Manufacturing of Image Pickup Device Chip

A plurality of image pickup units 21, each comprised of a CCD or CMOS image sensor or the like, are formed on an obverse surface 20SA of a wafer made of a semiconductor such as silicone. A microlens group may be formed on each of the image pickup units 21. After forming a plurality of wirings (not shown) connected with each of the image pickup units 21 and so forth, a transparent optical wafer, e.g. a cover glass wafer is joined to the obverse surface 20SA with a transparent adhesive, not shown.

Further, the through wirings 23 are formed from a side of the reverse surface 20SB, and the plurality of junction terminals 22 connected with each of the image pickup units 21 via the through wirings 23 and wirings (not shown) are formed. Then, by cutting the wafer, a large amount of image pickup device chips 20 with the cover glasses joined are made in a lump. Besides, if the cover glass is unnecessary, the cover glass wafer is not joined.

Each of the image pickup device chips 20 of a type of a chip size package manufactured by the above method has the image pickup unit 21 on the obverse surfaces 20SA and the plurality of joint terminals 22, which are connected to the image pickup unit 21 via the respective through wirings 23, on the reverse surface 20SB. Besides, the wirings for connecting the image pickup unit 21 and the junction terminals 22 may be located on a side surface of the image pickup device chip 20.

<Step S12> Manufacturing of Wiring Board

The wiring board 30 with a substrate of polyimide on which a conductor layer made of cupper is formed has a substantially rectangular shape and a width narrower than the image pickup device chip 20, and the first terminals 31 and the second terminals 32 are disposed on the first primary surface 30SA on both sides with the central flexible portion 30F intervened in between. The first terminals 31 and the second terminals 32 are connected by wirings (not shown).

Since the wiring board 30 is one flexible wiring board, boundaries of the flexible portion 30F are not clearly defined. Besides, it may be configured that at least a center of the wiring board is flexible, and the wiring board may be a rigid flexible wiring board with both end portions constituted by rigid substrates.

Further, it is preferable that the wiring board 30 is a both-side wiring board having a conductor layer formed on an approximately entire surface of the second primary surface 30SB for improving heat transmission efficiency, as described later. Further, the wiring board 30 may be a multilayer wiring board.

Besides, it is needless to say that the order of the image pickup device chip manufacturing step (S11) and the wiring board manufacturing step (S12) may be reversed.

<Step S13> Joining of Image Pickup Device Chip

Figure 6:
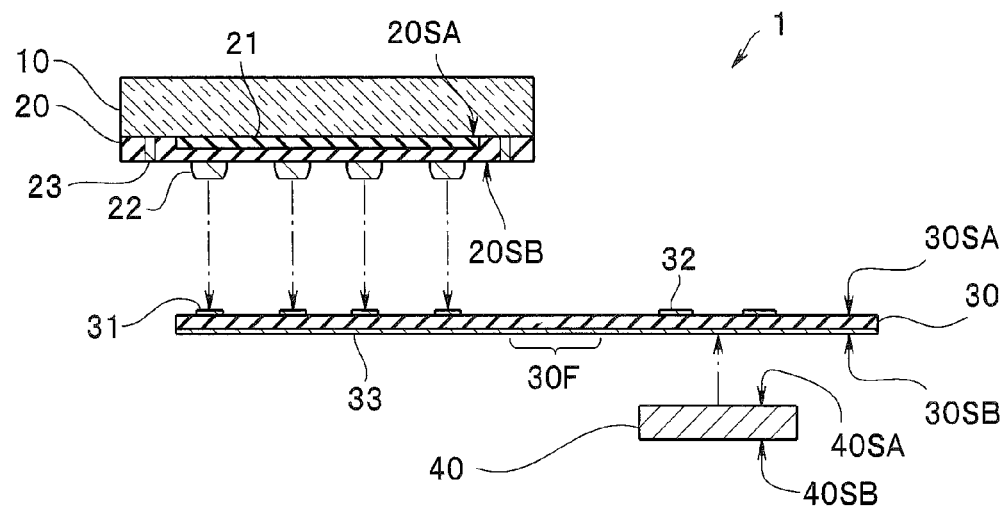
FIG. 6 is a cross sectional view for explaining the manufacturing method of the image pickup apparatus according to the first embodiment.

As shown in FIG. 6, the junction terminals 22 of the image pickup device chip 20 are joined to the first terminals 31 of the wiring board 30 in a planar state. It is preferable that a space between the image pickup device chip 20 and the wiring board 30 is sealed with sealing resin (not shown). A gold bump, a solder ball, an ACP (anisotropic conductive plastic), an ACF (anisotropic conductive film) or the like may be used for joining the junction terminals 22 and the first terminals 31.

<Step S14> Joining of Heat Conductive Block

As shown in FIG. 6, a first junction surface 40SA of the heat conductive block 40 is joined to the second primary surface 30SB of the wiring board 30 in the planar state. The heat conductive block 40 in a substantially rectangular parallelepiped shape is made of a material having thermal conductivity $\lambda$ not lower than 20 $Wm^{-1}K^{-1}$, for example, Cu ($\lambda$=398 $Wm^{-1}K^{-1}$), Si ($\lambda$=168 $Wm^{-1}K^{-1}$), Al ($\lambda$=236 $Wm^{-1}K^{-1}$), Fe ($\lambda$=84 $Wm^{-1}K^{-1}$) or SUS ($\lambda$=20 $Wm^{-1}K^{-1}$), or the like. As long as the thermal conductivity $\lambda$ is not lower than the above range, there is not any fear that the image pickup device chip 20 already joined is damaged by heat when joining the cable 50, as described later. Further, there is not any fear that an operation of the manufactured image pickup apparatus 1 is made unstable by the heat generated by the image pickup device chip 20.

A joining position of the heat conductive block 40 is set in a second region of the second primary surface 30SB which is opposite to a first region of the first primary surface 30SA in which the plurality of second terminals 32 are disposed. The image pickup apparatus 1 has an ultra-small size so as to be disposed at a distal end portion of an endoscope, as described later. Further, the first region (the second region) is small to have rectangular dimensions of several millimeters.

Further, the heat conductive block 40 has substantially the same dimensions as the first region (the second region) and is small to have rectangular dimensions of several millimeters. Therefore, it is possible to easily position the heat conductive block 40 with respect to the second region with high precision (e.g. mounting precision of ±35 μm) by using an electronic part mounting apparatus (mounter), for example.

The heat conductive block 40 is joined by soldering to a conductor layer 33 of the second primary surface 30SB of the wiring board 30, for example.

It is noted that the order of the image pickup device chip joining step (S13) and the heat conductive block joining step (S14) may be reversed.

<Step S15> Cable Joining

Figure 7:
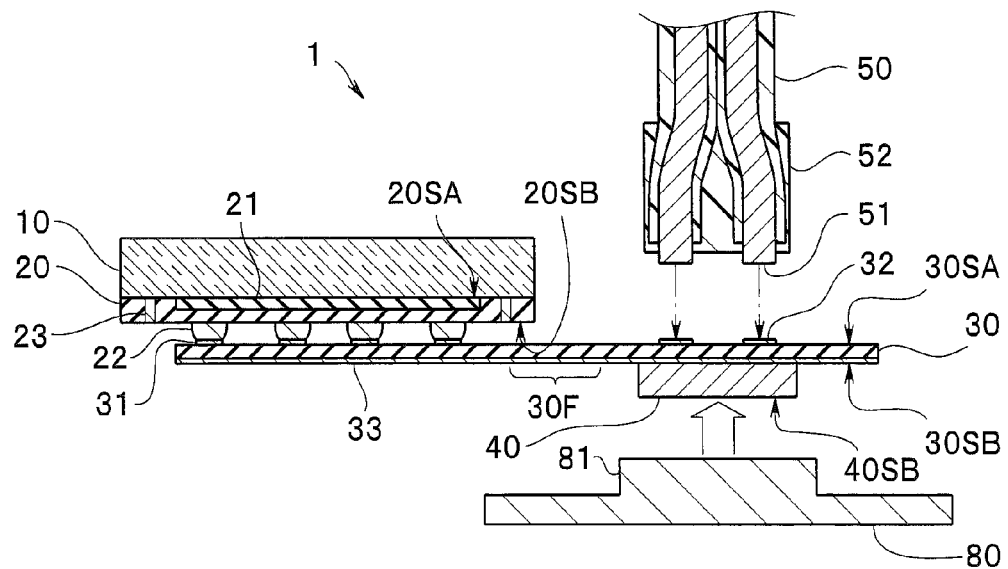
FIG. 7 is a cross sectional view for explaining the manufacturing method of the image pickup apparatus according to the first embodiment.

As shown in FIG. 7, the core wires 51 of the cable 50 are positioned to align with the second terminals 32 of the wiring board 30. On the other hand, a heat tool 80 having a heating portion 81 which is heated to have a soldering temperature is positioned to meet with the position of the heat conductive block 40, and is pressed and arranged on a second junction surface 40SB of the heat conductive block 40. When the heat tool 80 is heated to have the soldering temperature, solder (not shown) disposed between the core wires 51 and the second terminals 32 is melted, and thereby the wires 51 and the terminals 32 are joined.

Here, since the heat tool 80 is large and heavy, it is not easy to precisely position the heating portion 81 at a position of the second region of the wiring board 30. Further, an area of the heating portion 81 is larger than an area of junctions of the second terminals 32 and the core wires 51 which require heating. Therefore, if the heating portion 81 of the heat tool 80 is brought into direct contact with the wiring board 30, there is a fear that regions distant from the junctions are heated or the junctions are not sufficiently heated.

Figure 8:
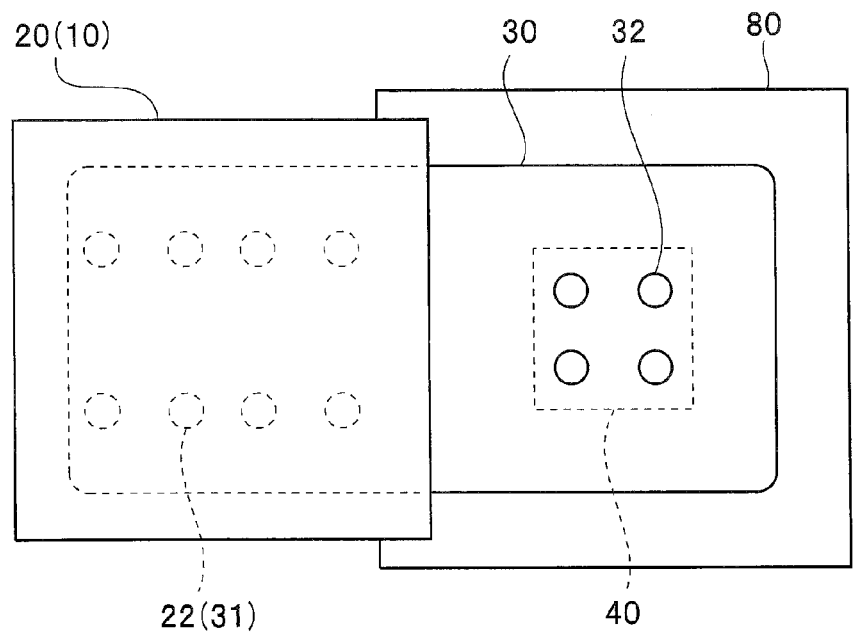
FIG. 8 is a top view for explaining the manufacturing method of the image pickup apparatus according to the first embodiment.

However, as shown in FIG. 8, in the manufacturing method according to the present embodiment, the heat conductive block 40 is jointed in advance on a back surface (in the second region) of the junctions (in the first region). Therefore, the heating portion 81 of the heat tool 80 does not come in contact with the wiring board 30 but comes in contact with the heat conductive block 40. The heat generated by the heat tool 80 is conducted to the junctions through the heat conductive block 40, and therefore only the junctions (in the first region) can be heated even if the heat tool 80 is not precisely positioned with respect to the second region.

It is noted that if the heat conductive block 40 is soldered to the wiring board 30, as the solder for joining the second terminals 32 and the core wires 51, a material having a lower melting point than the solder for joining the heat conductive block 40 is used.

Further, it is preferable that a plurality of cables 50 are bundled by the binding member 52 so that the core wires 51 are positioned to meet with arrangement positions of the corresponding second terminals 32 of the wiring board 30 in order to improve the workability.

<Step S16> Bending

The wiring board 30 is bent at the flexible portion 30F. In the manufacturing method of the image pickup apparatus 1, the wiring board is easily bent by 180 degrees only by being bent such that the second primary surface 30SB of the wiring board 30 is brought into contact with the second junction surface 40SB of the heat conductive block 40, which is opposite to the first junction surface 40SA. It is noted that the length of the wiring board 30 is designed such that the wiring board is arranged within a projected plane of the image pickup device chip 20 when the wiring board is bent, as already described.

The second junction surface 40SB of the heat conductive block 40 and the second primary surface 30SB of the wiring board 30 are joined with an adhesive intervened, or joined by sealing resin around the heat conductive block 40, as described later, and thereby the wiring board 30 is fixed in a state of being bent.

<Step S17> Resin Sealing

The image pickup device chip 20, the wiring board 30 (the heat conductive block 40) and the cable 50, which are integrated, are disposed inside the frame member 70 made of metal, and are sealed with the sealing resin 71, to complete the image pickup apparatus 1.

Besides, it is preferable that the frame member 70 is made of a metal having thermal conductivity 2 not lower than 10 $Wm^{-1}K^{-1}$, such as SUS in view of heat radiation. Further, it is preferable that the sealing resin 71 is a high thermal conductivity resin in which silicon or the like is dispersed. However, the sealing resin 71, even in a case of the high thermal conductivity resin, has thermal conductivity $\lambda$ at a degree of 1-10 $Wm^{-1}K^{-1}$.

Therefore, the heat generated by the image pickup device chip 20 is not sufficiently conducted only through the sealing resin 71. However, in the image pickup apparatus 1, the heat generated by the image pickup device chip 20 is conducted also to the cable 50 through the heat conductive block 40 which has the higher thermal conductivity than the sealing resin 71. Therefore, the image pickup apparatus 1 is stable in operation in comparison with a conventional image pickup apparatus with no heat conductive block.

It is noted that if the thermal conductivity of the heat conductive block 40 is equal to or more than twice the thermal conductivity of the sealing resin 71, or preferably equal to or more than five times the thermal conductivity of the sealing resin 71, the advantageous effect is remarkable.

Second Embodiment

Next, an image pickup apparatus 1A and a manufacturing method of the image pickup apparatus 1A according to a second embodiment will be described. Since the image pickup apparatus 1A and so forth are similar to the image pickup apparatus 1 and so forth, the same reference signs are assigned to the elements having the same functions and the description thereof is omitted.

Figure 9:
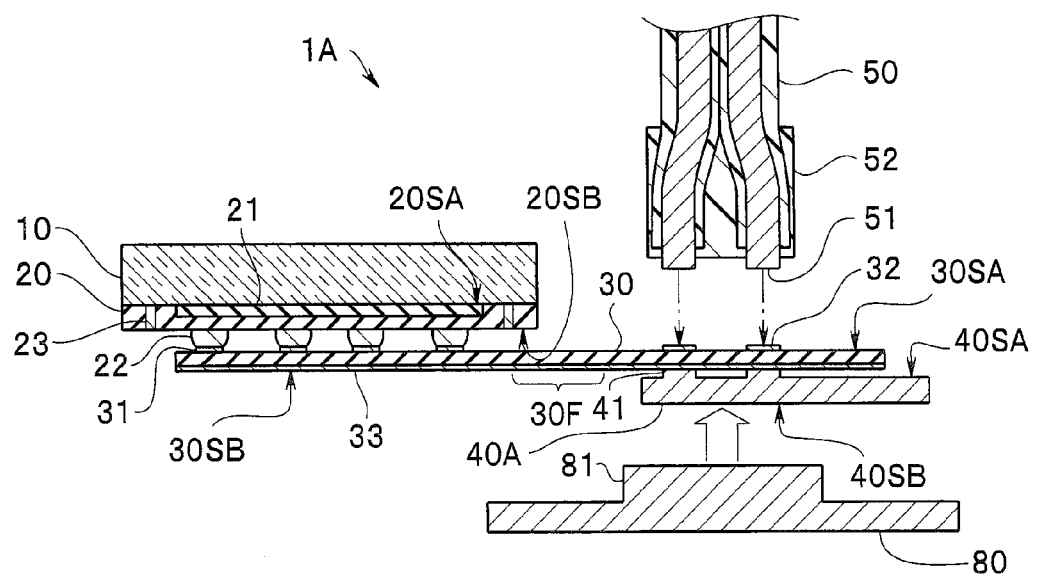
FIG. 9 is a cross sectional view for explaining a manufacturing method of an image pickup apparatus according to a second embodiment.
Figure 10:
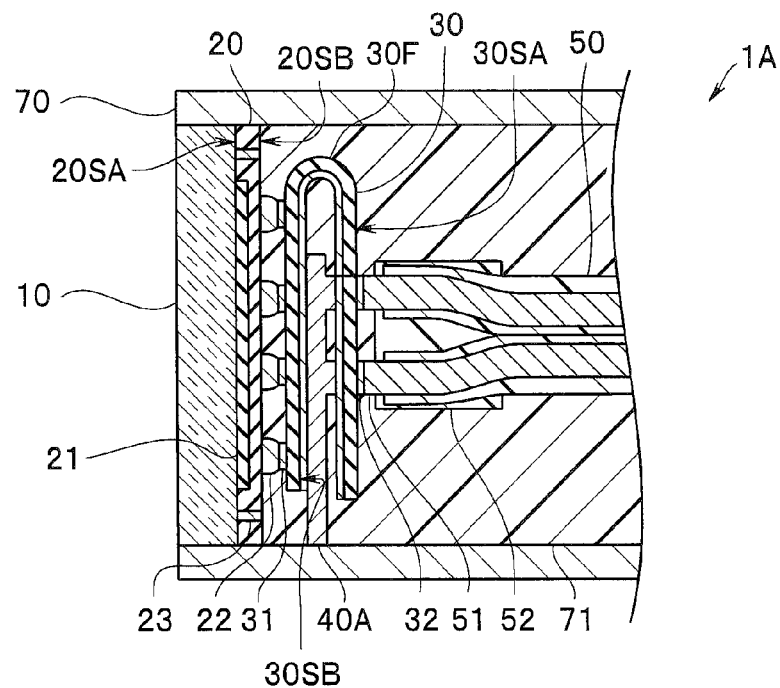
FIG. 10 is a cross sectional view of the image pickup apparatus according to the second embodiment.

As shown in FIGS. 9 and 10, there are a plurality of convex portions 41 on the first junction surface 40SA of a heat conductive block 40A of an image pickup apparatus 1A. The heat conductive block 40A is joined at a position such that the respective convex portions 41 are opposed to the second terminals 32 of the wiring board 30. The convex portions 41 have substantially the same sizes as the second terminals 32.

In the manufacturing method of the image pickup apparatus 1A, only the junctions of the second terminals 32 and the core wires 51, which are smaller than the first region, can be heated locally even if the heat tool 80 is not precisely positioned with respect to the second region.

Thus, according to the manufacturing method of the image pickup apparatus 1A, the joining can be performed more securely in addition to the advantageous effect of the manufacturing method of the image pickup apparatus 1.

Further, in the image pickup apparatus 1A of the present embodiment, dimensions of the heat conductive block 40A when viewed in a plan view are larger than the dimensions of the heat conductive block 40, when viewed in the plan view, of the image pickup apparatus 1 of the first embodiment. That is, the dimensions of the heat conductive block 40A in the plan view are larger than the dimensions of the first region (the second region). Further, a side surface of the heat conductive block 40A is in contact with the frame member 70.

Therefore, in the image pickup apparatus 1A, the heat generated by the image pickup device chip 20 is conducted to the frame member 70 through the heat conductive block 40A. Thus, the image pickup apparatus 1A is further stable in operation than the image pickup apparatus 1.

Third Embodiment

Next, an image pickup apparatus 1B and a manufacturing method of the image pickup apparatus 1B according to a third embodiment will be described using FIGS. 11 and 12. Since the image pickup apparatus 1B and so forth are similar to the image pickup apparatus 1 and so forth, the same reference signs are assigned to the elements having the same functions and the description thereof is omitted.

Figure 11:
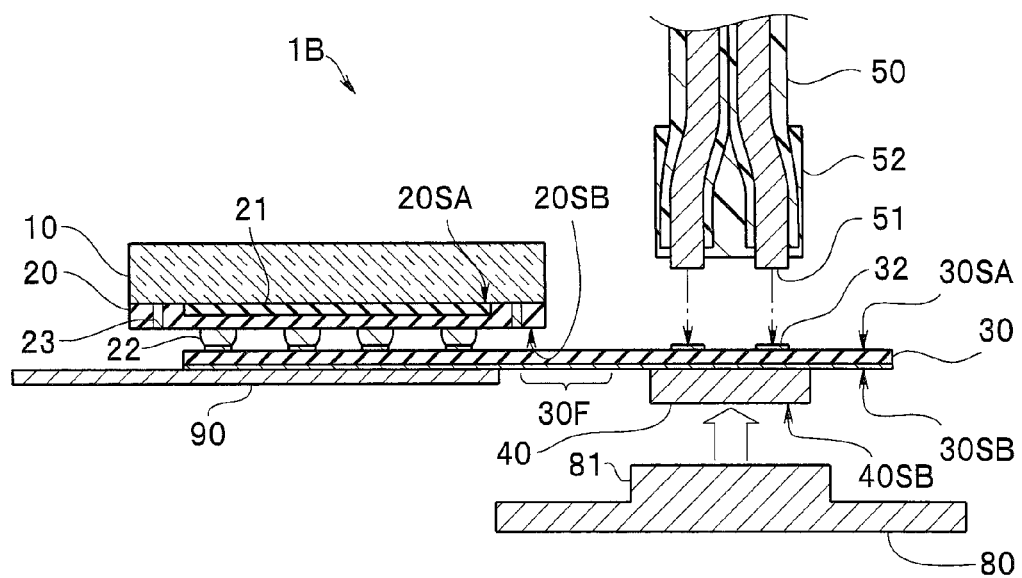
FIG. 11 is a cross sectional view for explaining a manufacturing method of an image pickup apparatus according to a third embodiment.

As shown in FIG. 11, the manufacturing method of the image pickup apparatus 1B further includes a step of joining a part of a band-shaped heat radiation member 90 to the second primary surface 30SB of the wiring board 30 in a first terminal opposing region which is opposed to a region on the first primary surface 30SA where the junction terminals 22 are disposed, prior to the step of soldering the core wires 51.

The heat radiation member 90 is made of a material having thermal conductivity not lower than 20 $Wm^{-1}K^{-1}$, such as copper foil. Therefore, when heat is applied to the wiring board 30 in the cable joining step, temperatures of the junctions of the image pickup device chip 20 and the wiring board 30, which are already joined, and the image pickup device chip 20 are hard to rise. It is noted that the effect is made more remarkable by cooling an extended portion of the heat radiation member 90.

Figure 12:
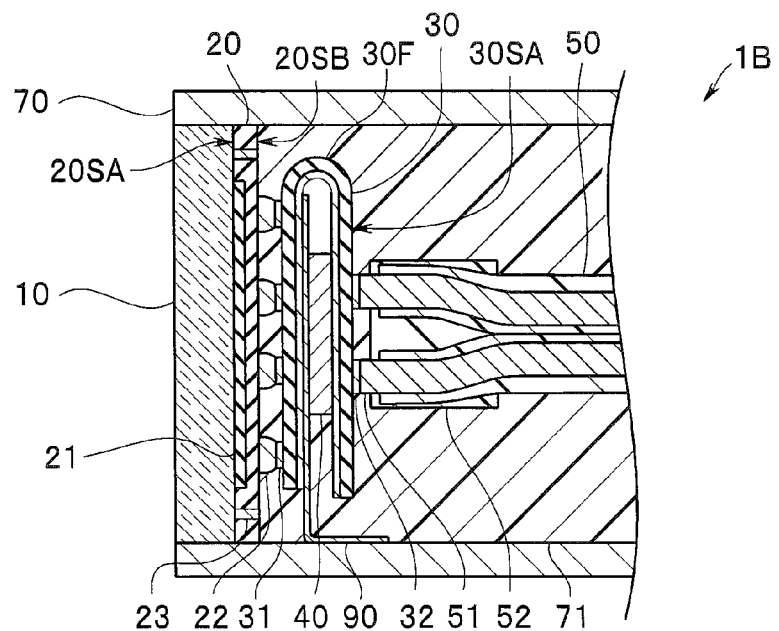
FIG. 12 is a cross sectional view of the image pickup apparatus according to the third embodiment.

Further, as shown in FIG. 12, in the manufactured image pickup apparatus 1B, a part of the heat radiation member 90 is sandwiched by the heat conductive block 40 and the wiring board 30, and the extended portion is joined to the frame member 70.

Therefore, in the image pickup apparatus 1B, the heat generated by the image pickup device chip 20 is conducted to the frame member 70 through the heat radiation member 90. Thus, the image pickup apparatus 1B is further stable in operation than the image pickup apparatus 1.

Fourth Embodiment

Figure 13:
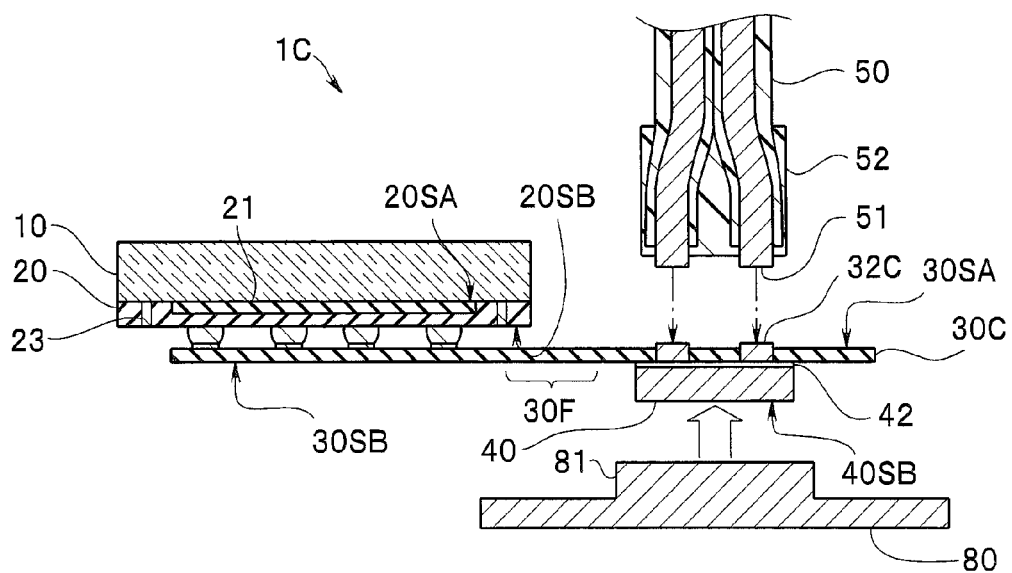
FIG. 13 is a cross sectional view for explaining a manufacturing method of an image pickup apparatus according to a fourth embodiment.

Next, an image pickup apparatus 1C and a manufacturing method of the image pickup apparatus 1C according to a fourth embodiment will be described using FIG. 13. The image pickup apparatus 1C and so forth are similar to the image pickup apparatus 1 and so forth, the same reference signs are assigned to the elements having the same functions and the description thereof is omitted.

In a wiring board 30C of the image pickup apparatus 1C, bottom faces of second terminals 32C pierce the wiring board 30C and are exposed on the second primary surface 30SB. The heat conductive block 40 is joined to the wiring board 30C through an insulating layer 42. It is noted that the insulating layer 42 is unnecessary in a case where the heat conductive block 40 is an insulator and the second terminals 32C are joined not to be short-circuited. Further, the convex portions 41 may be provided on the heat conductive block 40 in the same manner as in the second embodiment.

In the image pickup apparatus 1C, only the junctions of the second terminals 32C and the core wires 51, which are smaller than the first region, can be heated locally even if the heat tool 80 is not precisely positioned with respect to the second region.

Thus, the manufacturing method of the image pickup apparatus 1C has the same advantageous effect as the manufacturing method of the image pickup apparatus 1A.

Fifth Embodiment

Next, an endoscope 9 according to a fifth embodiment will be described.

Figure 14:
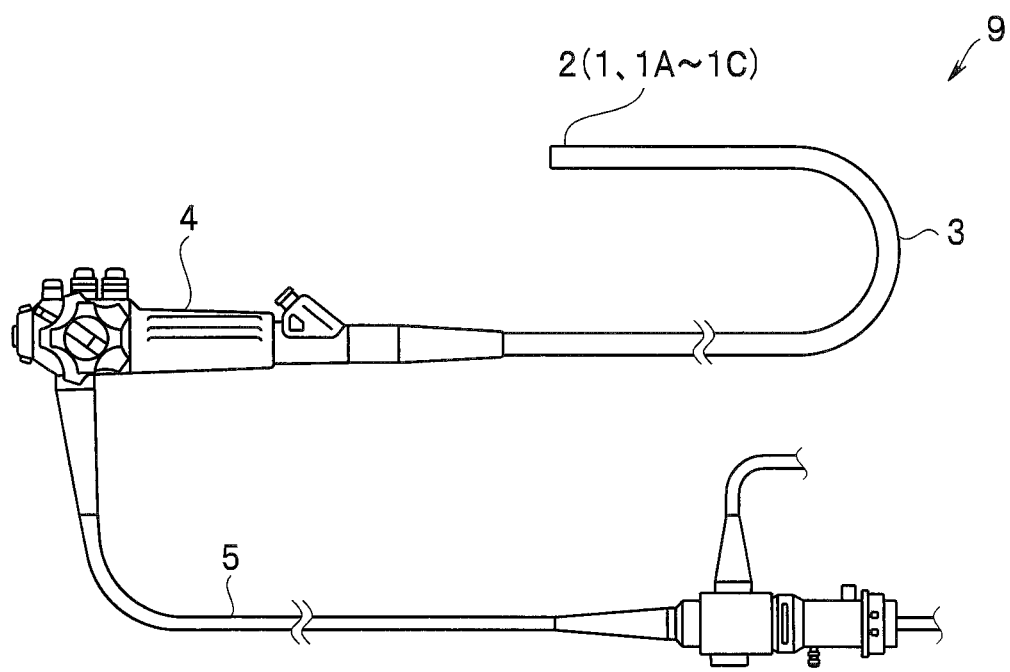
FIG. 14 is a view for explaining an endoscope according to a fifth embodiment.

As shown in FIG. 14, the endoscope 9 is comprised of an insertion portion 3 in which the image pickup apparatus 1, 1A-1C is disposed at a distal end portion 2, an operation portion 4 disposed at a proximal end side of the insertion portion 3, and a universal cord 5 extending from the operation portion 4.

Since the endoscope 9 includes the image pickup apparatus 1, etc. having high connection reliability between the image pickup device chip 20 and the cable 50, the endoscope 9 has high reliability. Further, since the heat generated by the image pickup device chip 20 is effectively radiated through the heat conductive block 40, the operation is stable.

Besides, in the foregoing description, the image pickup apparatus 1, etc. as a semiconductor apparatus are described as examples, but the semiconductor apparatus is not limited to the image pickup apparatus.

The present invention is not limited to the above-described embodiments, etc. and may be subjected to various changes, modifications, combinations and the like in a range in which the gist of the present invention is not changed.

What is claimed is:

1. A manufacturing method of a semiconductor apparatus, comprising:
    a step of manufacturing a semiconductor device chip having a semiconductor device unit on an obverse surface and junction terminals on a reverse surface, the junction terminals being connected with the semiconductor device unit via through wirings;
    a step of manufacturing a wiring board having a rectangular shape and a width smaller than a width of the semiconductor device chip, the wiring board having first terminals and second terminals on a first primary surface, the first terminals disposed on a first end of the first primary surface and the second terminals being disposed on a second end of the first primary surface with a flexible portion intervened in between;
    a step of joining a first junction surface of a heat conductive block to a second primary surface of the wiring board in a second terminal opposing region which is opposite to a region in which the second terminals are disposed on the first primary surface of the wiring board in a planar state, the heat conductive block being made of a material having thermal conductivity not lower than 20 $Wm^{-1}K^{-1}$;
    a step of joining the junction terminals of the semiconductor device chip to the first terminals of the wiring board in the planar state;
    a step of performing solder joining of core wires of a signal cable to the second terminals of the wiring board by conducting heat generated by a heat tool, which is heated to have a soldering temperature, through the heat conductive block;
    a step of bending the wiring board at the flexible portion such that a second junction surface of the heat conductive block which is opposite to the first junction surface comes in contact with the second primary surface of the wiring board, and arranging the wiring board within a projected plane of the semiconductor device chip; and
    a step of housing the semiconductor device chip, the wiring board, the heat conductive block, and the signal cable, which are integrated, inside a frame member made of metal, and sealing the semiconductor device chip, the wiring board, the heat conductive block and the signal cable with sealing resin.

2. The manufacturing method of a semiconductor apparatus according to claim 1, wherein the heat conductive block is housed inside the frame member such that a side surface of the heat conductive block is in contact with the frame member.

3. The manufacturing method of a semiconductor apparatus according to claim 1, further comprising a step of joining a part of a heat radiation member in a belt shape to the second primary surface of the wiring board in a first terminal opposing region which is opposite to a region in which the first terminals are disposed on the first primary surface of the wiring board, the heat radiation member being made of a material having thermal conductivity not lower than 20 $Wm^{-1}K^{-1}$, before the step of performing the solder joining of the core wires.

4. The manufacturing method of a semiconductor apparatus according to claim 1, wherein the semiconductor apparatus is an image pickup apparatus having the semiconductor device unit as an image pickup unit.

5. A semiconductor apparatus, comprising:
    a semiconductor device chip having a semiconductor device unit on an obverse surface and junction terminals on a reverse surface, the junction terminals being connected with the semiconductor device unit via through wirings;
    a signal cable having core wires electrically connected with the semiconductor device unit;
    a wiring board having a rectangular shape and a width smaller than a width of the semiconductor device chip, the wiring board having first terminals joined to the junction terminals and second terminals on a first primary surface, the first terminals disposed on a first end of the first primary surface and the second terminals and second terminals being disposed on a second end of the first primary surface with a flexible portion intervened in between, the second terminals being joined to the core wires of the signal cable by soldering, the wiring board being bent at the flexible portion to be in a state where the first primary surface and the second primary surface are parallel;
    a heat conductive block sandwiched by the second primary surface of the wiring board that is bent, and made of a material having thermal conductivity not lower than 20 $Wm^{-1}K^{-1}$; and
    a frame member in which the semiconductor device chip, the wiring board, the heat conductive block and the signal cable are housed, the frame member being made of metal and an inside of the frame member being sealed with sealing resin.

6. The semiconductor apparatus according to claim 5, wherein the heat conductive block has convex portions at positions opposite to the second terminals on the first junction surface in contact with the wiring board.

7. The semiconductor apparatus according to claim 5, wherein a side surface of the heat conductive block is in contact with the frame member.

8. The semiconductor apparatus according to claim 5, further comprising a heat radiation member in a belt shape, a part of the heat radiation member being sandwiched by the heat conductive block and the wiring board, an extending portion of the heat radiation member being joined to the frame member, and the heat radiation member being made of a material having thermal conductivity not lower than 20 $Wm^{-1}K^{-1}$.

9. The semiconductor apparatus according to claim 5, wherein the semiconductor apparatus is an image pickup apparatus having the semiconductor device unit as an image pickup unit.

10. An endoscope comprising an image pickup apparatus at a distal end portion of an insertion portion, the image pickup apparatus comprising:

an image pickup device chip having an image pickup unit on an obverse surface and junction terminals on a reverse surface, the junction terminals being connected with the image pickup unit via through wirings;

a signal cable having core wires electrically connected with the image pickup unit;

a wiring board having a rectangular shape and a width smaller than a width of the image pickup device chip, the wiring board having first terminals joined to the junction terminals and second terminals on a first primary surface, the first terminals disposed on a first end of the first primary surface and second terminals being disposed on a second end of the first primary surface with a flexible portion intervened in between, the second terminals being joined to the core wires of the signal cable by soldering, the wiring board being bent at the flexible portion to be in a state where the first primary surface and the second primary surface are parallel;

a heat conductive block sandwiched by the second primary surface of the wiring board that is bent, and made of a material having thermal conductivity not lower than 20 $Wm^{-1}K^{-1}$; and a frame member in which the image pickup device chip, the wiring board, the heat conductive block and the signal cable are housed, the frame member being made of metal and an inside of the frame member being sealed with sealing resin.

\* \* \* \* \*